United States Patent [19]

Láng et al.

[11] Patent Number: 4,614,740

[45] Date of Patent: Sep. 30, 1986

[54] 5H-2,3-BENZODIAZEPINE DERIVATIVES AND PHARMACEUTICAL COMPOSITIONS CONTAINING THE SAME

[75] Inventors: Tibor Láng; Jeno Korösi; Ferenc Andrási; Péter Botka; Tamás Hámori; Pál Berzsenyi; Katalin Goldschmidt; Gábor Zólyomi; István Elekes; Zsuzsanna Láng née Rihmer, all of Budapest, Hungary

[73] Assignee: Egis Gyogyszergyar, Budapest, Hungary

[21] Appl. No.: 759,169

[22] Filed: Jul. 26, 1985

[30] Foreign Application Priority Data

Jul. 27, 1984 [HU] Hungary ............... 2251/2882/84

[51] Int. Cl.⁴ .................. A61K 31/35; C07D 243/00
[52] U.S. Cl. .................................. 514/221; 540/567
[58] Field of Search ............... 260/239 BD; 514/221

[56] References Cited

U.S. PATENT DOCUMENTS

| Re. 30,014 | 5/1929 | Korosi et al. | 260/239 BD |
| 3,736,315 | 5/1973 | Korosi et al. | 260/239 BD |
| 4,322,346 | 3/1982 | Korosi et al. | 260/239 BD |
| 4,423,044 | 12/1983 | Korosi et al. | 260/239 BD |

*Primary Examiner*—Robert T. Bond
*Attorney, Agent, or Firm*—Keil & Weinkauf

[57] ABSTRACT

The invention relates to new 5H-2,3-benzodiazepine derivatives and a process for the preparation thereof, furthermore to pharmaceutical compositions containing the same.

The new 5H-2,3-benzodiazepine derivatives of the invention possess valuable central nervous effect and in particular exert antiaggressive, anxiolytic, narcosis potentiating and soporific properties.

7 Claims, No Drawings

5H-2,3-BENZODIAZEPINE DERIVATIVES AND PHARMACEUTICAL COMPOSITIONS CONTAINING THE SAME

This invention relates to new 5H-2,3-benzodiazepine derivatives and a process for the preparation thereof, furthermore to pharmaceutical compositions containing the same.

According to a feature of the present invention there are provided new 5H-2,3-benzodiazepine derivatives corresponding to the general formula I and pharmaceutically acceptable acid addition salts thereof,

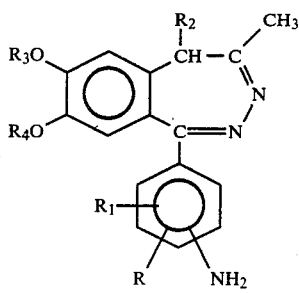

wherein
R and $R_1$ each represent hydrogen, chlorine, $C_{1-4}$ alkyl or $C_{1-4}$ alkoxy,
$R_2$ stands for hydrogen or $C_{1-4}$ alkyl,
$R_3$ and $R_4$ each denote $C_{1-4}$ alkyl, or combined they denote methylene.

In the foregoing definitions the term "$C_{1-4}$ alkyl" covers straight-chained or branched saturated aliphatic hydrocarbyl groups of from one to four carbon atom(s) e.g. methyl, ethyl, n-propyl, isopropyl, etc. The term "$C_{1-4}$ alkoxy" refers to straight-chained or branched alkoxy groups containing one to four carbon atoms(s) e.g. methoxy, ethoxy, n-propoxy, isopropoxy, etc.

Preferred representatives of the compounds having the general formula I are those described in the Examples.

Particularly preferred representatives of the compounds according to the invention are the following derivatives:

1-(4-aminophenyl)-4-methyl-7,8-dimethoxy-5H-2,3-benzodiazepine,
1-(3-aminophenyl)-4-methyl-7,8-dimethoxy-5H-2,3-benzodiazepine,
1-(3-methyl-4-aminophenyl)-4-methyl-7,8-dimethoxy-5H-2,3-benzodiazepine,
1-(3-chloro-4-aminophenyl)-4-methyl-7,8-dimethoxy-5H-2,3-benzodiazepine,
1-(4-aminophenyl)-4-methyl-7,8-methylenedioxy-5H-2,3-benzodiazepine,
and the pharmaceutically acceptable acid addition salts thereof.

The pharmaceutically acceptable acid addition salts of the compounds of the general formula I can be formed with inorganic or organic acids generally used for this purpose, e.g. with hydrogen chloride, hydrogen bromide, sulfuric, phosphoric, perchloric, maleic, fumaric, succinic, p-toluenesulfonic, lactic acid, etc.

The compounds of the general formula I have valuable pharmaceutical properties. They possess significant central nervous properties and in particular exert antiaggressive, anxiolytic, narcosis potentiating and hypnotic effects.

5-H-2,3-Benzodiazepines have already been described in the literature including U.S. Pat. No. 3,736,315 and Belgian patent specification No. 879,404, and the pharmaceutical properties of these derivatives show great differences from those of 1,4-benzodiazepines. Similarly to them the new 5H-2,3-benzodiazepines have no muscle relaxant nor spasmolytic effects and cause no coordination troubles either.

According to a further feature of the present invention there is provided a process for the preparation of the new compounds of the general formula I and pharmaceutically acceptable acid addition salts thereof, characterized by reducing a compound of the general formula II,

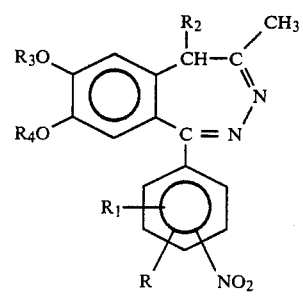

wherein R, $R_1$, $R_2$, $R_3$ and $R_4$ have the above-defined meanings, in an organic solvent, and, if desired, converting the thus-obtained compound of the general formula I into a pharmaceutically acceptable acid addition salt, or liberating a free base of the general formula I from its salt and converting it into another acid addition salt.

As organic solvent it is preferred to use a $C_{1-4}$ alcohol, dioxane, tetrahydrofurane, benzene, toluene, xylene, dimethylformamide, dimethylacetamide or a mixture thereof.

According to a preferred embodiment of the process according to the invention a compound of the general formula II is dissolved in dimethylformamide and subjected to catalytical hydrogenation. The reaction is preferably performed at room temperature. As catalyst, palladium on bone coal, platinum or Raney nickel can be used.

The reaction mixture can be worked up by known methods, e.g. by filtering off the catalyst, evaporating the solvent in vacuo and purifying the residue by recrystallization and/or digeration. For the recrystallization preferably lower alcohols can be used.

In the above reaction only the nitro group of the 5H-2,3-benzodiazepines of the general formula II is reduced, in contradiction to the 1,4-benzodiazepines, in which the C=N double bond of similar position is saturated by catalytical hydrogenation [J. Org. Chem. 28, 2456 1963; Coll. Czech. Chem. Comm. 31, 1264 /1966/].

According to another preferred embodiment of the process according to the invention the starting compounds of the general formula II are suspended in a lower alcohol and reduced with hydrazine or hydrazine hydrate, in the presence of a catalyst. For this reaction 98 to 100% hydrazine hydrate and, as catalyst, palladium on bone coal, platinum or Raney nickel are preferably used. The reduction can be performed at a temperature between room temperature and the boiling point of the solvent. The reaction mixture is worked up by known methods.

It is particularly preferable to carry out the reduction with hydrazine hydrate in case of compounds containing chlorine substituents [Chem. Rev. 65, 51 1965].

Besides the above-specified methods, the nitro compounds of the general formula II can be reduced by any known method which causes no change in the structure of the diazepine ring. E.g. complex metal hydrides can not be used as reducing agent, because in addition to the reduction of the nitro group the saturation of the double bond between the nitrogen atom in position 3 and the carbon atom in position 4 also takes place U.S. Pat. No. 4,423,044. When reducing with porous zinc in glacial acetic acid, the 7-membered ring of the 5H-2,3-benzodiazepines is converted into a 6-membered ring, that is isoquinoline derivatives are obtained [Chem. Ber. 107, 3883 1974/].

In the above reactions the compounds of the general formula I are obtained as bases. The salts thereof are preferably formed by dissolving or suspending the base in an appropriate solvent, e.g. in methanol, ethanol, isopropanol, glacial acetic acid or water, and adding to the solution a suitable acid, e.g. hydrogen chloride, hydrogen bromide, phosphoric acid, sulfuric acid or a solution thereof in an appropriate solvent. The salts are separated by filtration or distillation and, if desired, converted again into other acid addition salts.

Some crude bases can not be purified by direct recrystallization, so it is preferable to liberate the base from a pure acid addition salt. The bases of the general formula I can be liberated from their salts e.g. by dissolving the given salt in water, rendering the solution alkaline with an organic base, such as triethylamine or pyridine, or with an inorganic base, such as aqueous sodium hydroxide or ammonium hydroxide solution, and filtering off the liberated base. The pure base obtained in this way can be converted, if desired, into another acid addition salt.

Among the starting compounds of the general formula II there are known and new derivatives. They can be produced preferably from the corresponding 2-benzopyrilium salts or 1,5-diketones, respectively, with hydrazine or hydrazine hydrate Belgian patent specification No. 879,404.

The new 5H-2,3-benzodiazepine derivatives of the invention possess valuable central nervous effects, e.g. antiaggressive, anxiolytic, narcosis potentiating and hypnotic effects. The strength of their activity surpasses considerably those of the 1-(3-chlorophenyl)-4-methyl-7,8-dimethoxy-5H-2,3-benzodiazepine (U.S. Pat. No. 4,322,346) and tofizopam [Grandaxin, 1-(3,4-dimethoxyphenyl)-4-methyl-5-ethyl-7,8-dimethoxy-5H-2,3-benzodiazepine] used in the therapy. While tofizopam has, in addition to the anxiolytic effect, a weak antidepressant activity, the new compounds according to the invention are of slightly neuroleptic character. So these compounds can be used as ingredients of daytime tranquillizers to cure anguish and psychical tension.

The antiaggressive effect was studied on mice by the so-called "fighting behaviour" test [J. Pharm. Exp. Ther. 125, 28 (1959)]. Tofizopam and 1-(3-chlorophenyl)-4-methyl-7,8-dimethoxy-5H-2,3-benzodiazepine were used as reference agents. The results are given in Table I.

TABLE I

| Compound /No. of Example/ | $ED_{50}$ mg/kg p.o. | Relative activity |
|---|---|---|
| 1 | 8.1 | 7.9 |
| 2 | 12.5 | 5.1 |
| 10 | 9.1 | 7.0 |
| 11 | 16.0 | 4.6 |
| 15 | 17.0 | 3.8 |
| 18 | 7.9 | 8.1 |
| Tofizopam | 74.0 | 1.0 |
| 1-(3-chlorophenyl)-4-methyl-7,8-dimethoxy-5H—2,3-benzodiazepine | 16.0 | 4.6 |

The anxiolytic effect was determined by the method of Vogel lick-conflict test/[Psychopharmacol. 21, 1 1979]. Tofizopam, 1-(3-chlorophenyl)-4-methyl-7,8-dimethoxy-5H-2,3-benzodiazepine and Chlorodiazepoxide 7-chloro-2-methylamino-5-phenyl-3H-1,4-benzodiazepine-4-oxide were used as reference agents. The data obtained are summarized in Table II.

TABLE II

| Compound No. of Example | Dose mg/kg i.p. | Number of animals | Number of electric shocks tolerated | Significance |
|---|---|---|---|---|
| Vehiculum | — | 6 | 2.3 ± 0.4 | not significant |
| 1 | 2.5 | 10 | 4.1 ± 0.7 | |
| Vehiculum | — | 23 | 2.8 ± 0.3 | $p < 0.001$ |
| 1 | 5 | 22 | 13.9 ± 2.7 | |
| Vehiculum | — | 20 | 4.4 ± 0.7 | $p < 0.001$ |
| 1 | 10 | 21 | 19.7 ± 2.9 | |
| Vehiculum | — | 5 | 3.2 ± 0.6 | not significant |
| 2 | 10 | 10 | 4.2 ± 0.7 | |
| Vehiculum | — | 10 | 5.5 ± 1.1 | $p < 0.001$ |
| 2 | 25 | 17 | 15.1 ± 1.9 | |
| Vehiculum | — | 8 | 3.3 ± 0.5 | not significant |
| 18 | 2.5 | 8 | 7.6 ± 3.0 | |
| Vehiculum | — | 15 | 4.9 ± 0.94 | $p < 0.05$ |
| 18 | 5 | 20 | 8.3 ± 1.0 | |
| Vehiculum | — | 60 | 4.5 ± 0.4 | not significant |
| Tofizopam | 25 | 10 | 3.6 ± 0.4 | |
| | 50 | 16 | 19.8 ± 3.7 | $p < 0.001$ |
| Chlorodiazepoxide | 5 | 10 | 9.7 ± 3.7 | not significant |
| | 10 | 24 | 27.5 ± 2.5 | $p < 0.001$ |
| 1-(3-chlorophenyl)-4-methyl-7,8-dimethoxy-5H—2,3-benzodiazepine | 25 | 13 | 9.9 ± 2.8 | not significant |
| | 50 | 24 | 19.0 ± 2.3 | $p < 0.001$ |

The spontaneous motor activity was measured on a motimeter of Animex type. Groups of animal consisting of 3 mice from the CFLP strain weighing 20 to 23 g were starved for 24 hours and put to the apparatus. After a previous treatment of 10 minutes the amount of movements was registered continuously for 2 hours. The dose decreasing the spontaneous motor activity to half in comparison with the control group treated with vehiculum was determined.

The $ED_{50}$ values were calculated by the method of Litchfield and Wilcoxon [J. Pharmacol. Exp. Ther. 96, 99 1949]. The results obtained are given in Table III.

TABLE III

| Compound No. of Example | $ED_{50}$ value mg/kg p.o. |
|---|---|
| 1 | 3.2/1.8–5.9/ |
| 2 | 1.3/0.6–2.8/ |
| 8 | 48.0/37.8–61.0/ |
| 10 | 4.4/3.7–5.2/ |
| 15 | 9.7/6.7–14.1/ |
| Tofizopam | 22.0/16.4–29.5/ |

TABLE III-continued

| Compound No. of Example | ED$_{50}$ value mg/kg p.o. |
|---|---|
| 1-(Chlorophenyl)-4-methyl-7,8-dimethoxy-5H—2,3-benzodiazepine | 6.2/4.0–9.7 |

The narcosis potentiating effect was studied on mice. The compounds were administered in 3 or 4 oral doses to 15–20 animals per dose. Narcosis was induced with 50 mg/kg of sodium hexobarbital injected intravenously into the animals. The ED$_{50}$ value is the dose increasing the narcosis period of half of the test animals to double. The data obtained are given in Table IV.

TABLE IV

| Compound No. of Example | ED$_{50}$ mg/kg p.o. |
|---|---|
| 1 | 4.8 /3.4–6.6/ |
| 2 | 8.2 /5.4–12.5/ |
| 8 | 7.4 /4.8–11.3/ |
| 10 | 7.4 /5.6–9.7/ |
| 15 | 25.0 /18.2–34.2/ |
| 18 | 7.6 /5.5–10.4/ |
| Tofizopam | 38 |
| 1-(Chlorophenyl)-4-methyl-7,8-dimethoxy-5H—2,3-benzodiazepine | 16 |

The data of the above Tables clearly demonstrate that the efficiencies of the compounds according to the invention achieve or considerably surpass those of the reference substances.

1-(4-Aminophenyl)-4-methyl-7,8-methylendioxy-5H-2,3-benzodiazepine compound of Example 8 possesses significant hypnotic activity, its HD$_{50}$ values determined in mice being 140 mg/kg p.o., 70 mg/kg i.p. and 40 mg/kg i.v. and in rats being 40 mg/kg i.v. The HD$_{50}$ values of Nitrazepam (7-nitro-5-phenyl-1,3-dihydro-2H-1,4-benzodiazepin-2-one) in mice are 185 mg/kg p.o., 150 mg/kg i.p. and 75 mg/kg i.v. while in rats it is 96 mg/kg i.v.

The compounds of the general formula I wherein R$_3$ and R$_4$ stand together for a methylene group possess, unlike the other compounds of the general formuala I, considerable muscle relaxant and spasmolytic activity, too. Thus 1-(4-aminophenyl)-4-methyl-7,8-methylene-dioxy-5H-2,3-benzodiazepine compound of Example 8, a muscle relaxant with central point of attack, is more potent than the reference substance Zoxazolamine 2-amino-5-chloro-1,3-benzoxazole. Their ED$_{50}$ values amount to 47 and >100 mg/kg i.p. in the "inclined screen" test [J. Pharm. Exp. 129, 163 1960], and to 24 and 74 mg/kg i.p. in the rotarod test [J. of Am. Pharm. Assoc. 46, 208 1957].

According to a further feature of the present invention there are provided new pharmaceutical compositions containing as active ingredient at least one compound of the general formula I or a pharmaceutically acceptable acid addition salt thereof, together with one or more pharmaceutical carrier(s), diluent(s) and/or additive(s). The pharmaceutical compositions may contain also other biologically active substances, particularly other anxiolytic agents.

The pharmaceutical compositions can be formulated in solid such as tablets, coated tablets, capsules, etc. or in liquid forms such as solutions, suspensions, emulsions, etc. The carrier may be such as generally used in pharmacy e.g. starch, magnesium stearate, magnesium carbonate, talc, stearin, gelatin, lactose, cellulose, calcium carbonate, polyvinyl pyrrolidone, water, polyalkylene glycol, etc. The compositions may also contain suitable additives e.g. suspending, emulsifying, stabilizing agents, buffers, etc. and therapeutically valuable further agents.

The compositions can be presented in the form of orally, parenterally or rectally administerable preparations.

The pharmaceutical compositions can be prepared by methods generally applied in the pharmaceutical industry.

The daily dose of the new compounds according to the invention is about 25 to 70 mg, the accurate dose being dependent on the body weight, age and general health condition of the patient.

The invention is elucidated in detail by the aid of the following non-limiting Examples.

EXAMPLE 1

Preparation of 1-(4-aminophenyl)-4-methyl-7,8-dimethoxy-5H-2,3-benzodiazepine 26.6 g (0.078 mole) of 1-(4-nitrophenyl)-4-methyl-7,8-dimethoxy-5H-2,3-benzodiazepine are suspended in 540 ml of dimethylformamide, 2 g of 10% palladium on bone coal catalyst are suspended in 60 ml of dimethylformamide and added to the previous suspension. The reaction mixture is stirred vigorously at room temperature, under hydrogen. The reduction terminates in about 15 hours. Then the catalyst is filtered off, the filtrate is clarified with activated carbon and evaporated in vacuo. The crystalline residue is boiled with 250 ml of ethanol for one hour. Then it is cooled, the crystals are filtered off, washed twice with 30 ml of ethanol each and dried at 80° to 100° C.

Yield: 21.5 g (89%).

M.p.: 225° to 227° C. $C_{18}H_{19}N_3O_2 = 309.374$.

The hydrochloride salts are prepared in the way as follows:

1 g of base is dissolved in 5 ml of glacial acetic acid, and anhydrous ethanol saturated with the calculated amount of gasous hydrogen chloride are added to the solution. The separated crystals are filtered off and washed with ethyl acetate.

Monochlorohydrate: $[C_{18}H_{20}N_3O_2]Cl = 345.839$.

M.p.: 237° to 238° C. (decomp.).

Analysis: calculated Cl % = 10.25. found Cl % = 10.4.

Dichlorohydrate: $[C_{18}H_{21}N_3O_2]Cl_2 = 382.304$.

M.p.: 236° to 238° C. (decomp.).

Analysis: calculated Cl% = 18.55. found Cl% = 18.3.

The sulfate salt is prepared as follows:

1 g of base is dissolved in water and a calculated amount of concentrated sulfuric acid is added to it. The solution is evaporated, the residue is taken up in hot isopropanol. The crude product is recrystallized from glacial acetic acid.

$(C_{18}H_{20}N_3O_2)_2SO_4 = 716.830$.

M.p.: 235° to 237° C. (decomp.).

Analysis: calculated SO$_4$% = 13.40. found SO$_4$% = 13.55.

The compounds according to Examples 2 to 7 were prepared by the method described in Example 1.

EXAMPLE 2

1-(3-Aminophenyl)-4-methyl-7,8-dimethoxy-5H-2,3-benzodiazepine $C_{18}H_{19}N_3O_2 = 309.374$.
M.p.: 213° to 215° C. (from 50% ethanol).
Monochlorohydrate: $[C_{18}H_{20}N_3O_2]Cl = 345.839$.
M.p.: 195° to 198° C. (decomp.).
Dichlorohydrate: $[C_{18}H_{21}N_3O_2]Cl_2 = 382.304$.
M.p.: 217° to 218° C. (from isopropanol) (decomp.).

EXAMPLE 3

1-(2-Aminophenyl)-4-methyl-7,8-dimethoxy-5H-2,3-benzodiazepine

M.p.: 172° to 174° C. (from aqueous dimethylformamide, then suspended in ethanol).
Dichlorohydrate: M.p.: 174° to 176° C. (decomp.) (from isopropanol).

EXAMPLE 4

1-(3-Aminophenyl)-4-methyl-7,8-diethoxy-5H-2,3-benzodiazepine

M.p.: 133° to 134° C. (from the mixture of ethanol and water).

EXAMPLE 5

1-(3-Aminophenyl)-4-methyl-7,8-methylenedioxy-5H-2,3-benzodiazepine

M.p.: 190° to 191° C. (from the mixture of ethanol and water)

EXAMPLE 6

1-(2-Amino-4,5-dimethoxyphenyl)-4-methyl-7,8-dimethoxy-5H-2,3-benzodiazepine

M.p.: 194° to 196° C. from the mixture of dimethylformamide and water.

EXAMPLE 7

1-(2-Aminophenyl)-4-methyl-7,8-methylenedioxy-5H-2,3-benzodiazepine

M.p.: 171° to 173° C. from ethanol.

EXAMPLE 8

Preparation of 1-(4-aminophenyl)-4-methyl-7,8-methylenedioxy-5H-2,3-benzodiazepine To a suspension of 1.52 g (0.0047 mole) of 1-(4-nitrophenyl)-4-methyl-7,8-methylenedioxy-5H-2,3-benzodiazepine in 45 ml of methanol 0.2 g 10% palladium on bone coal catalyst and 0.7 ml (0.014 mole) of 100% hydrazine hydrate are added, and the reaction mixture is stirred at room temperature for 6 hours. Then it is warmed up to 50° to 60° C., the catalyst is filtered off and washed thrice with 10 ml of methanol each. The filtrate is evaporated in vacuo and the residue is recrystallized repeatedly from 5 ml of 99.5% ethanol. Yield: 1.05 g (76%). M.p.: 235° to 236° C.

The compounds according to Examples 9 to 12 were prepared by the method described in Example 8. Methanol, ethanol or dioxane were used as reaction medium, and the reduction was carried out at the boiling point of the solvents too.

EXAMPLE 9

1-(2-Amino-5-chlorophenyl)-4-methyl-7,8-dimethoxy-5H-2,3-benzodiazepine

M.p.: 190° to 192° C. suspended in ethanol.

EXAMPLE 10

1-(3-Methyl-4-aminophenyl)-4-methyl-7,8-dimethoxy-5H-2,3-benzodiazepine

M.p.: 192° to 194° C. from isopropanol.

EXAMPLE 11

1-(4-Aminophenyl)-4,5-dimethyl-7,8-dimethoxy-5H-2,3-benzodiazepine

M.p.: 188° to 190° C. suspended in ethanol.

EXAMPLE 12

1-(4-Aminophenyl)-4-methyl-5-ethyl-7,8-dimethoxy-5H-2,3-benzodiazepine

M.p.: 166° to 168° C. liberated from its dichlorohydrate salt in water.

EXAMPLE 13

Preparation of 1-(2-chloro-4-aminophenyl)-4-methyl-7,8-dimethoxy-5H-2,3-benzodiazepine A mixture of 4.10 g (0.011 mole) of 1-(2-chloro-4-nitrophenyl)-4-methyl-7,8-dimethoxy-5H-2,3-benzodiazepine, 100 ml of methanol, 0.4 g of Raney nickel catalyst and 1.2 ml (0.025 mole) of 98% hydrazine hydrate is stirred for one hour. The temperature of the reaction mixture rises first 40° to 50° C. then cools to room temperature. When the reduction has already been terminated, the mixture is warmed up to 40° to 50° C., the catalyst is filtered off and washed twice with 10 ml of chloroform each. The filtrate is evaporated in vacuo and the residue is boiled in 20 ml of ethanol for 2 hours. Then it is cooled, the separated crystals are filtered off, washed thrice with 3 ml of ethanol each and dried at 60° to 100° C.

Yield: 3.3 g /87%/.
M.p.: 218° to 220° C. decomp.

The compounds according to the Examples 14 to 18 were prepared by the method described in Example 13, with the difference that ethanol, isopropanol or dioxane were used instead of methanol, and the reduction was performed at higher temperatures.

EXAMPLE 14

1-(3-Amino-4-chlorophenyl)-4-methyl-7,8-dimethoxy-5H-2,3-benzodiazepine

M.p.: 214° to 215° C. (decomp.) (from the mixture of dimethylformamide and water and suspended in ethanol).

EXAMPLE 15

1-(3-Amino-4-methylphenyl)-4-methyl-7,8-dimethoxy-5H-2,3-benzodiazepine

M.p.: 197° to 199° C. (decomp.) (suspended in ethanol).

EXAMPLE 16

1-(2-Chloro-5-aminophenyl)-4-methyl-7,8-dimethoxy-5H-2,3-benzodiazepine

M.p.: 188° to 190° C. from the mixture of dimethylformamide and water and suspended in ethanol.

EXAMPLE 17

1-(4-Aminophenyl)-4-methyl-7,8-diethoxy-5H-2,3-benzodiazepine

M.p.: 133° to 135° C. suspended in ethanol.

EXAMPLE 18

1-(3-Chloro-4-aminophenyl)-4-methyl-7,8-dimethoxy-5H-2,3-benzodiazepine

M.p.: 173° to 175° C. suspended in ethanol.

EXAMPLE 19

Preparation of a pharmaceutical composition

Dragées containing 20.0 mg of 1-(4-aminophenyl)-4-methyl-7,8-dimethoxy-5H-2,3-benzodiazepine are prepared in a manner known per se. The composition of a dragée kernel is as follows:

| | |
|---|---|
| Active ingredient | 20.0 mg |
| Lactose | 122.0 mg |
| Maize starch | 20.5 mg |
| Cellulose microcrystalline | 10.0 mg |
| Gelatin | 3.5 mg |
| Talc | 2.0 mg |
| Stearine | 1.0 mg |
| Magnesium stearate | 1.0 mg |
| | 180.0 mg |

What we claim is:

1. A 5H-2,3-Benzodiazepine of the formula I and pharmaceutically acceptable acid addition salts thereof,

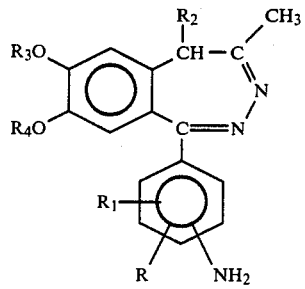

wherein
$R$ and $R_1$ each represent hydrogen, chlorine, $C_{1-4}$ alkyl or $C_{1-4}$ alkoxy,
$R_2$ stands for hydrogen or $C_{1-4}$ alkyl,
$R_3$ and $R_4$ each denote $C_{1-4}$ alkyl, or combined they denote methylene.

2. A compound selected from the group consisting of 1-(4-aminophenyl)-4-methyl-7,8-dimethoxy-5H-2,3-benzodiazepine, 1-(3-aminophenyl)-4-methyl-7,8-dimethoxy-5H-2,3-benzodiazepine, 1-4-aminophenyl)-4-methyl-7,8-methylenedioxy-5H-2,3-benzodiazepine, 1-(3-methyl-4-aminophenyl)-4-methyl-7,8-dimethoxy-5H-2,3-benzodiazepine, 1-(3-chloro-4-aminophenyl)-4-methyl-7,8-dimethoxy-5H-2,3-benzodiazepine and pharmaceutically acceptable acid addition salts of these compounds.

3. The compound of the formula I of claim 1 which is 1-(4-aminophenyl)-4-methyl-7,8-dimethoxy-5H-2,3-benzodiazepine.

4. The compound of the formula I of claim 1 which is 1-(4-aminophenyl)-4-methyl-7,8-methylenedioxy-5H-2,3-benzodiazepine.

5. A pharmaceutical composition for exerting antiaggresive, anxiolytic, narcosis potentiating and hypnotic effects which comprises: an effective amount of at least one compound of the formula I as defined in claim 1 or a pharmaceutically acceptable acid addition salt thereof, together with one or more pharmaceutically carrier(s), diluent(s) and/or additives.

6. A pharmaceutical composition as defined in claim 5, wherein the compound of the formula I is 1-(4-aminophenyl)-4-methyl-7,8-dimethoxy-5H-2,3-benzodiazepine.

7. A pharmaceutical composition as defined in claim 5, wherein the compound of the formula I is 1-(4-aminophenyl)-4-methyl-7,8-methylenedioxy-5H-2,3-benzodiazepine.

* * * * *